(12) United States Patent
Buchberger

(10) Patent No.: US 10,918,820 B2
(45) Date of Patent: Feb. 16, 2021

(54) INHALER COMPONENT

(71) Applicant: BATMark Limited, London (GB)

(72) Inventor: Helmut Buchberger, Ennsdorf (AT)

(73) Assignee: Batmark Limited, London (GB)

( * ) Notice: Subject to any disclaimer, the term of this patent is extended or adjusted under 35 U.S.C. 154(b) by 432 days.

(21) Appl. No.: 15/997,113

(22) Filed: Jun. 4, 2018

(65) Prior Publication Data
US 2018/0280653 A1   Oct. 4, 2018

Related U.S. Application Data

(63) Continuation of application No. 14/268,909, filed on May 2, 2014, now Pat. No. 10,010,695, which is a (Continued)

(30) Foreign Application Priority Data

Feb. 11, 2011   (AT) ..................................... 187/2011
Jul. 27, 2011   (AT) ................................... 1095-2011

(51) Int. Cl.
*A61M 16/14*   (2006.01)
*A24F 47/00*   (2020.01)
(Continued)

(52) U.S. Cl.
CPC ......... *A61M 16/145* (2014.02); *A24F 47/008* (2013.01); *A61M 11/041* (2013.01);
(Continued)

(58) Field of Classification Search
None
See application file for complete search history.

(56) References Cited

U.S. PATENT DOCUMENTS 228,598 A    6/1880   Buckley
353,327 A   11/1886   Randolph
(Continued)

FOREIGN PATENT DOCUMENTS

AT    507 187 B1    3/2010
AT     507187 A4    3/2010
(Continued)

OTHER PUBLICATIONS

Application and File History for U.S. Appl. No. 14/787,946, filed Oct. 29, 2015, inventor Lord.
(Continued)

*Primary Examiner* — Rachel T Sippel
(74) *Attorney, Agent, or Firm* — Patterson Thuente Pedersen, P.A.

(57) ABSTRACT

The invention relates to an inhaler component for forming a vapor-air mixture and/or condensation aerosol by vaporizing a liquid material and optionally condensing the vapor formed, including: a heating element for vaporizing a portion of the liquid material; a wick for automatically supplying the liquid material to the heating element, wherein the wick includes at least two end sections arranged apart from each other; a first capillary gap for automatically supplying the liquid material to the wick, wherein a first end section of the wick projects into the first capillary gap. In order that the heating element can be supplied more quickly and more reliably with the liquid material, a second capillary gap is provided, which receives therein the second end section of the wick.

14 Claims, 8 Drawing Sheets

Related U.S. Application Data continuation of application No. 13/984,512, filed as application No. PCT/AT2012/000017 on Feb. 2, 2012, now Pat. No. 8,752,545.

(51) Int. Cl.

| | | |
|---|---|---|
| *A61M 11/04* | (2006.01) | |
| *A61M 15/06* | (2006.01) | |
| *B05B 7/00* | (2006.01) | |
| *B05B 7/16* | (2006.01) | |
| *A61M 15/00* | (2006.01) | |
| *H05K 1/02* | (2006.01) | |
| *A61M 16/10* | (2006.01) | |
| *A61M 15/08* | (2006.01) | |

(52) U.S. Cl.
CPC .......... *A61M 11/042* (2014.02); *A61M 15/00* (2013.01); *A61M 15/0021* (2014.02); *A61M 15/06* (2013.01); *A61M 16/109* (2014.02); *A61M 16/1075* (2013.01); *A61M 16/14* (2013.01); *B05B 7/0012* (2013.01); *B05B 7/168* (2013.01); *B05B 7/1686* (2013.01); *H05K 1/0272* (2013.01); *A61M 15/08* (2013.01); *A61M 2205/3606* (2013.01); *A61M 2205/3653* (2013.01); *A61M 2205/8206* (2013.01); *H05K 1/0298* (2013.01)

(56) References Cited

U.S. PATENT DOCUMENTS

| | | |
|---|---|---|
| 576,653 A | 2/1897 | Bowlby |
| 595,070 A | 12/1897 | Oldenbusch |
| 744,074 A | 11/1903 | Hiering |
| 799,844 A | 9/1905 | Fuller |
| 885,374 A | 4/1908 | Pohlig |
| 1,163,183 A | 12/1915 | Stoll |
| D53,386 S | 5/1919 | Thomas |
| 1,436,157 A | 11/1922 | Fazio |
| 1,807,936 A | 6/1931 | Saunders |
| 1,815,069 A | 7/1931 | Petro |
| 1,937,120 A | 11/1933 | Lagerholm |
| 1,937,987 A | 12/1933 | Sexton |
| 2,057,353 A | 10/1936 | Whittemore |
| 2,262,318 A | 11/1941 | Fox |
| 2,411,946 A | 12/1946 | Vogel |
| 2,467,923 A | 4/1949 | Allen |
| 2,483,304 A | 9/1949 | Vogel |
| 2,522,952 A | 9/1950 | Krohn |
| 2,658,368 A | 11/1953 | Siegal |
| 2,782,910 A | 2/1957 | Liebow |
| 2,809,634 A | 10/1957 | Murai |
| 3,111,396 A | 11/1963 | Ball |
| 3,165,225 A | 1/1965 | Reitzel |
| 3,402,724 A | 9/1968 | Blount et al. |
| 3,431,393 A | 3/1969 | Katsuda |
| 3,433,632 A | 3/1969 | Elbert et al. |
| 3,521,643 A | 7/1970 | Toth |
| 3,604,428 A | 9/1971 | Moukaddem |
| 3,722,742 A | 3/1973 | Wertz |
| 3,743,136 A | 7/1973 | Chambers |
| 3,804,100 A | 4/1974 | Fariello |
| 3,861,523 A | 1/1975 | Fountain et al. |
| 3,863,803 A | 2/1975 | Valcic |
| 3,964,902 A | 6/1976 | Fletcher |
| 4,009,713 A | 3/1977 | Simmons |
| 4,031,906 A | 6/1977 | Knapp |
| 4,094,119 A | 6/1978 | Sullivan |
| 4,145,001 A | 3/1979 | Weyenberg |
| 4,161,283 A | 7/1979 | Hyman |
| 4,190,412 A | 2/1980 | Tokai |
| 4,193,513 A | 3/1980 | Bull, Jr. |
| 4,214,658 A | 7/1980 | Crow |
| 4,503,851 A | 3/1985 | Brauroth |
| D279,508 S | 7/1985 | Bauer et al. |
| 4,588,976 A | 5/1986 | Jaselli |
| 4,676,237 A | 6/1987 | Wood |
| 4,677,992 A | 7/1987 | Bliznak |
| 4,733,794 A | 3/1988 | Kent |
| 4,735,217 A | 4/1988 | Gerth |
| 4,753,383 A | 6/1988 | Focke et al. |
| 4,793,478 A | 12/1988 | Tudor |
| 4,830,028 A | 5/1989 | Lawson |
| 4,848,374 A | 7/1989 | Chard |
| 4,885,129 A | 12/1989 | Leonard |
| 4,917,301 A | 4/1990 | Munteanu |
| 4,922,901 A | 5/1990 | Broooks |
| 4,923,059 A | 5/1990 | Evers et al. |
| 4,947,874 A | 8/1990 | Brooks |
| 4,947,875 A | 8/1990 | Brooks et al. |
| 4,978,814 A | 12/1990 | Honour |
| 5,027,837 A | 7/1991 | Clearman |
| 5,044,550 A | 9/1991 | Lamm |
| 5,046,514 A | 9/1991 | Bolt |
| 5,060,671 A | 10/1991 | Counts et al. |
| D322,687 S | 12/1991 | Tschudin |
| 5,095,647 A | 3/1992 | Zobele |
| 5,095,921 A | 3/1992 | Losee et al. |
| 5,096,921 A | 3/1992 | Bollinger |
| 5,099,861 A | 3/1992 | Clearman et al. |
| 5,121,881 A | 6/1992 | Lembeck |
| 5,167,242 A | 12/1992 | Turner |
| 5,179,966 A | 1/1993 | Losee |
| 5,247,947 A | 9/1993 | Clearman et al. |
| 5,269,327 A | 12/1993 | Counts et al. |
| D346,878 S | 5/1994 | Gee et al. |
| 5,322,075 A | 6/1994 | Deevi |
| 5,388,574 A | 2/1995 | Ingebrethsen |
| 5,390,864 A | 2/1995 | Alexander |
| 5,408,574 A | 4/1995 | Deevi et al. |
| 5,448,317 A | 9/1995 | Huang |
| 5,479,948 A | 1/1996 | Counts |
| 5,497,792 A | 3/1996 | Prasad |
| 5,501,236 A | 3/1996 | Hill |
| 5,505,214 A | 4/1996 | Collins |
| 5,530,225 A | 6/1996 | Hajaligol |
| 5,540,241 A | 7/1996 | Kim |
| 5,553,791 A | 9/1996 | Alexander |
| 5,636,787 A | 6/1997 | Gowhari |
| 5,649,554 A | 7/1997 | Murphy |
| 5,659,656 A | 8/1997 | Das |
| 5,666,977 A | 9/1997 | Higgins et al. |
| 5,692,291 A | 12/1997 | Seetharama |
| D392,069 S | 3/1998 | Rowland |
| 5,743,251 A | 4/1998 | Howell et al. |
| D404,201 S | 1/1999 | Wennerstrom |
| 5,865,185 A | 2/1999 | Collins et al. |
| 5,875,968 A * | 3/1999 | Miller ............ A61L 9/127 239/44 |
| 5,878,722 A | 3/1999 | Gras et al. |
| 5,878,752 A | 3/1999 | Adams et al. |
| 5,896,984 A | 4/1999 | Focke |
| D414,892 S | 10/1999 | Chen |
| 5,967,312 A | 10/1999 | Jacobs |
| 6,040,560 A | 3/2000 | Fleischhauer et al. |
| 6,058,711 A | 5/2000 | Maciaszek et al. |
| 6,065,592 A | 5/2000 | Wik |
| 6,095,505 A | 8/2000 | Miller |
| D432,263 S | 10/2000 | Issa |
| D434,217 S | 11/2000 | Packard et al. |
| D434,979 S | 12/2000 | Liu |
| 6,155,268 A | 12/2000 | Manabu |
| D436,725 S | 1/2001 | Rogers |
| D438,003 S | 2/2001 | Minagawa et al. |
| D441,133 S | 4/2001 | Emery |
| 6,275,650 B1 | 8/2001 | Lambert |
| D449,521 S | 10/2001 | Pinkus et al. |
| 6,321,757 B1 | 11/2001 | McCutcheon |
| 6,446,793 B1 | 9/2002 | Layshock |
| D466,012 S | 11/2002 | Baker |
| D470,765 S | 2/2003 | Baker |
| D471,804 S | 3/2003 | Staples |
| D472,012 S | 3/2003 | South |

(56) References Cited

U.S. PATENT DOCUMENTS

| | | |
|---|---|---|
| 6,527,166 B1 | 3/2003 | Focke et al. |
| 6,530,495 B1 | 3/2003 | Joseph |
| 6,561,391 B1 | 5/2003 | Baker |
| 6,652,804 B1 | 11/2003 | Neumann et al. |
| 6,681,998 B2 | 1/2004 | Sharpe |
| 6,701,921 B2 | 3/2004 | Sprinkel |
| 6,715,605 B1 | 4/2004 | Manservigi et al. |
| D493,617 S | 8/2004 | Armato |
| 6,790,496 B1 | 9/2004 | Levander et al. |
| D509,732 S | 9/2005 | Staples |
| 7,100,618 B2 | 9/2006 | Dominguez |
| 7,112,712 B1 | 9/2006 | Ancell |
| D545,186 S | 6/2007 | Liebe et al. |
| D549,573 S | 8/2007 | Liebe et al. |
| 7,263,282 B2 | 8/2007 | Meyer |
| D550,455 S | 9/2007 | Barnhart |
| D566,329 S | 4/2008 | Bagaric et al. |
| D566,890 S | 4/2008 | Bagaric et al. |
| 7,389,878 B1 | 6/2008 | Torrico |
| D573,889 S | 7/2008 | Short et al. |
| 7,400,940 B2 | 7/2008 | McRae et al. |
| D575,451 S | 8/2008 | Jones et al. |
| 7,455,176 B2 | 11/2008 | Focke et al. |
| 7,540,286 B2 | 6/2009 | Cross et al. |
| 7,565,969 B2 | 7/2009 | He |
| D606,854 S | 12/2009 | Greenhalgh |
| D610,983 S | 3/2010 | Wai et al. |
| D611,806 S | 3/2010 | Bried |
| D613,903 S | 4/2010 | Wu |
| D613,904 S | 4/2010 | Wu |
| D616,753 S | 6/2010 | Beam et al. |
| 7,767,698 B2 | 8/2010 | Warchol |
| 7,832,410 B2 | 11/2010 | Hon |
| D628,469 S | 12/2010 | Taylor et al. |
| D631,838 S | 2/2011 | Cheng |
| D636,257 S | 4/2011 | Bougoulas et al. |
| 7,992,554 B2 | 8/2011 | Radomski |
| D649,658 S | 11/2011 | Belfrance et al. |
| D650,738 S | 12/2011 | Leung |
| 8,113,343 B2 | 2/2012 | Akerlind |
| D656,094 S | 3/2012 | Wu |
| 8,156,944 B2 | 4/2012 | Hon |
| D661,016 S | 5/2012 | Borges et al. |
| D671,677 S | 11/2012 | Wu |
| D671,678 S | 11/2012 | Wu |
| 8,307,834 B1 | 11/2012 | Palmerino, Sr. et al. |
| D672,642 S | 12/2012 | Supranowicz |
| D674,539 S | 1/2013 | Wu |
| 8,365,742 B2 | 2/2013 | Hon |
| 8,375,957 B2 | 2/2013 | Hon |
| 8,393,331 B2 | 3/2013 | Hon |
| 8,430,106 B2 | 4/2013 | Potter et al. |
| 8,448,783 B2 | 5/2013 | Vecchi |
| 8,490,628 B2 | 7/2013 | Hon |
| 8,511,318 B2 | 8/2013 | Hon |
| D693,055 S | 10/2013 | Manca et al. |
| D700,397 S | 2/2014 | Manca et al. |
| 8,752,545 B2 | 6/2014 | Buchberger |
| 8,689,805 B2 | 8/2014 | Hon |
| 8,794,245 B1 | 8/2014 | Scatterday |
| 8,833,364 B2 | 9/2014 | Buchberger |
| D715,760 S | 10/2014 | Kim et al. |
| D716,267 S | 10/2014 | Kim et al. |
| 8,910,640 B2 | 12/2014 | Sears et al. |
| D720,884 S | 1/2015 | Liu |
| 8,948,578 B2 | 2/2015 | Buchberger |
| D723,738 S | 3/2015 | Liu |
| 9,055,617 B2 | 6/2015 | Thorens et al. |
| D736,460 S | 8/2015 | McKeon et al. |
| D737,507 S | 8/2015 | Liu |
| 9,609,894 B2 | 4/2017 | Abramov |
| 9,623,205 B2 | 4/2017 | Buchberger |
| 9,730,276 B2 | 8/2017 | Vissa et al. |
| 9,961,939 B2 | 5/2018 | Reevell |
| 9,986,760 B2 | 6/2018 | Macko et al. |
| 10,010,695 B2 | 7/2018 | Buchberger |
| 10,045,562 B2 | 8/2018 | Buchberger |
| 2001/0042546 A1 | 11/2001 | Umeda et al. |
| 2002/0005207 A1 | 1/2002 | Wrenn |
| 2002/0016370 A1 | 2/2002 | Shytle |
| 2002/0079309 A1 | 6/2002 | Cox |
| 2003/0005620 A1 | 1/2003 | Shytle |
| 2003/0049025 A1 | 3/2003 | Neumann |
| 2003/0079309 A1 | 6/2003 | Cox |
| 2003/0106552 A1 | 6/2003 | Sprinkel |
| 2003/0108342 A1 | 6/2003 | Sherwood et al. |
| 2003/0168057 A1 | 9/2003 | Snyder et al. |
| 2003/0200964 A1 | 10/2003 | Blakely |
| 2003/0202169 A1 | 10/2003 | Liu |
| 2004/0031485 A1 | 2/2004 | Rustad |
| 2004/0056651 A1 | 3/2004 | Marietta |
| 2004/0129793 A1 | 7/2004 | Nguyen et al. |
| 2004/0210151 A1 | 10/2004 | Tsukashima et al. |
| 2004/0226568 A1 | 11/2004 | Takeuchi |
| 2005/0063686 A1 | 3/2005 | Whittle et al. |
| 2005/0087460 A1 | 4/2005 | Bruhm et al. |
| 2005/0145260 A1 | 7/2005 | Inagaki |
| 2005/0194013 A1 | 9/2005 | Wright |
| 2005/0204799 A1 | 9/2005 | Koch |
| 2005/0211243 A1 | 9/2005 | Esser |
| 2005/0224375 A1 | 10/2005 | Focke et al. |
| 2005/0268911 A1 | 12/2005 | Cross |
| 2006/0078477 A1 | 4/2006 | Althouse |
| 2006/0137681 A1 | 6/2006 | Von Hollen |
| 2007/0014549 A1 | 1/2007 | Demarest et al. |
| 2007/0045288 A1 | 3/2007 | Nelson |
| 2007/0062548 A1 | 3/2007 | Horstmann |
| 2007/0102013 A1 | 5/2007 | Adams |
| 2007/0107879 A1 | 5/2007 | Radomsnki |
| 2007/0155255 A1 | 7/2007 | Galauner |
| 2007/0193895 A1 | 8/2007 | Weiss et al. |
| 2007/0267031 A1 | 11/2007 | Hon |
| 2008/0017204 A1 | 1/2008 | Braunshteyn |
| 2008/0092912 A1 | 4/2008 | Robinson |
| 2008/0156326 A1 | 7/2008 | Belcastro et al. |
| 2008/0216828 A1 | 9/2008 | Wensley |
| 2008/0223382 A1 | 9/2008 | Zeanah |
| 2008/0241255 A1 | 10/2008 | Rose |
| 2009/0090472 A1 | 4/2009 | Radomski |
| 2009/0095311 A1 | 4/2009 | Han |
| 2009/0272379 A1 | 6/2009 | Thorens |
| 2009/0188490 A1 | 7/2009 | Han |
| 2009/0241947 A1 | 10/2009 | Bedini |
| 2009/0266837 A1 | 10/2009 | Gelardi et al. |
| 2009/0288966 A1 | 11/2009 | Minarelli et al. |
| 2009/0293892 A1 | 12/2009 | Williams |
| 2010/0059070 A1 | 3/2010 | Potter |
| 2010/0065653 A1 | 3/2010 | Potter |
| 2010/0083959 A1 | 4/2010 | Siller |
| 2010/0108059 A1 | 5/2010 | Axelsson et al. |
| 2010/0182608 A1 | 7/2010 | Zribi et al. |
| 2010/0236546 A1 | 9/2010 | Yamada |
| 2010/0242974 A1 | 9/2010 | Pan |
| 2010/0313901 A1 | 12/2010 | Fernando et al. |
| 2011/0011396 A1 | 1/2011 | Fang |
| 2011/0126848 A1 | 6/2011 | Zuber et al. |
| 2011/0155153 A1 | 6/2011 | Thorens et al. |
| 2011/0180433 A1 | 7/2011 | Rennecamp |
| 2011/0192914 A1 | 8/2011 | Ishigami |
| 2011/0226236 A1 | 9/2011 | Buchberger |
| 2011/0277757 A1 | 11/2011 | Terry et al. |
| 2011/0036363 A1 | 12/2011 | Urtsev |
| 2011/0290267 A1 | 12/2011 | Yamada |
| 2011/0297166 A1 | 12/2011 | Takeuchi |
| 2011/0303231 A1 | 12/2011 | Li |
| 2011/0309157 A1* | 12/2011 | Yang .......... A01M 1/2077 239/6 |
| 2012/0145169 A1 | 6/2012 | Wu |
| 2012/0199146 A1 | 8/2012 | Marangos |
| 2012/0227752 A1 | 9/2012 | Alelov |
| 2012/0227753 A1 | 9/2012 | Newton |
| 2012/0242974 A1 | 9/2012 | Lavalley et al. |
| 2012/0260927 A1 | 10/2012 | Liu |
| 2012/0285476 A1 | 11/2012 | Hon |

(56) References Cited

U.S. PATENT DOCUMENTS

| | | |
|---|---|---|
| 2013/0074857 A1 | 3/2013 | Buchberger |
| 2013/0081623 A1 | 4/2013 | Buchberger |
| 2013/0087160 A1 | 4/2013 | Gherghe |
| 2013/0098786 A1 | 4/2013 | Collins |
| 2013/0142782 A1 | 6/2013 | Rahmel |
| 2013/0192615 A1 | 8/2013 | Tucker |
| 2013/0192621 A1 | 8/2013 | Li |
| 2013/0192623 A1 | 8/2013 | Tucker |
| 2013/0213419 A1 | 8/2013 | Tucker |
| 2013/0255702 A1 | 10/2013 | Griffith, Jr. et al. |
| 2013/0284192 A1 | 10/2013 | Peleg |
| 2013/0319407 A1 | 12/2013 | Liu |
| 2013/0333700 A1 | 12/2013 | Buchberger |
| 2013/0340779 A1 | 12/2013 | Liu |
| 2013/0341218 A1 | 12/2013 | Liu |
| 2013/0342157 A1 | 12/2013 | Liu |
| 2014/0000638 A1 | 1/2014 | Sebastian |
| 2014/0007892 A1 | 1/2014 | Liu |
| 2014/0020697 A1 | 1/2014 | Liu |
| 2014/0048086 A1 | 2/2014 | Zhanghua |
| 2014/0060528 A1 | 3/2014 | Liu |
| 2014/0060554 A1 | 3/2014 | Collett |
| 2014/0060555 A1 | 3/2014 | Chang |
| 2014/0106155 A1 | 4/2014 | Iandoli Espinosa |
| 2014/0182608 A1 | 7/2014 | Egoyants |
| 2014/0196717 A1 | 7/2014 | Liu |
| 2014/0196731 A1 | 7/2014 | Scatterday |
| 2014/0202454 A1 | 7/2014 | Buchberger |
| 2014/0202476 A1 | 7/2014 | Egoyants |
| 2014/0209105 A1 | 7/2014 | Sears |
| 2014/0216485 A1 | 8/2014 | Egoyants |
| 2014/0238396 A1 | 8/2014 | Buchberger |
| 2014/0238423 A1 | 8/2014 | Tucker |
| 2014/0238424 A1 | 8/2014 | Macko et al. |
| 2014/0261490 A1 | 9/2014 | Kane |
| 2014/0261495 A1 | 9/2014 | Novak |
| 2014/0270726 A1 | 9/2014 | Egoyants |
| 2014/0270730 A1 | 9/2014 | DePiano |
| 2014/0283825 A1 | 9/2014 | Buchberger |
| 2014/0286630 A1 | 9/2014 | Buchberger |
| 2014/0299125 A1 | 10/2014 | Buchberger |
| 2014/0332019 A1 | 11/2014 | Liu |
| 2014/0338680 A1 | 11/2014 | Abramov et al. |
| 2015/0114411 A1 | 4/2015 | Buchberger |
| 2015/0128971 A1 | 5/2015 | Verleur et al. |
| 2015/0136756 A1 | 5/2015 | Vissa et al. |
| 2015/0157055 A1 | 6/2015 | Lord |
| 2015/0181934 A1 | 7/2015 | Lyubomirskiy et al. |
| 2015/0196058 A1 | 7/2015 | Lord |
| 2015/0208728 A1 | 7/2015 | Lord |
| 2016/0073693 A1 | 3/2016 | Reevell |
| 2016/0101909 A1 | 4/2016 | Schennum et al. |
| 2016/0106154 A1 | 4/2016 | Lord |
| 2016/0106155 A1 | 4/2016 | Reevell |
| 2016/0120218 A1 | 5/2016 | Schennum et al. |
| 2016/0278163 A1 | 9/2016 | Chen |
| 2017/0006916 A1 | 1/2017 | Liu |
| 2017/0042245 A1 | 2/2017 | Buchberger |
| 2017/0188629 A1 | 7/2017 | Dickens et al. |
| 2017/0197043 A1 | 7/2017 | Buchberger |
| 2017/0197044 A1 | 7/2017 | Buchberger |
| 2017/0197046 A1 | 7/2017 | Buchberger |

FOREIGN PATENT DOCUMENTS

| | | |
|---|---|---|
| AT | 507188 A4 | 3/2010 |
| AT | 508244 | 12/2010 |
| AT | 510 405 A4 | 4/2012 |
| AT | 510504 A1 | 4/2012 |
| AU | 63913/73 | 6/1975 |
| AU | 6393173 A | 6/1975 |
| BR | 6402132 | 7/1986 |
| CA | 2309376 | 11/2000 |
| CH | 698603 B1 | 9/2009 |
| CL | 199400288 A1 | 8/1995 |
| CL | 199900377 | 3/1999 |
| CN | 2092880 | 1/1992 |
| CN | 2220168 | 2/1996 |
| CN | 1205849 A | 1/1999 |
| CN | 1312730 A | 9/2001 |
| CN | 1329567 A | 1/2002 |
| CN | 2485265 | 4/2002 |
| CN | 2660914 | 12/2004 |
| CN | 1607911 A | 4/2005 |
| CN | 2719043 | 8/2005 |
| CN | 1694765 A | 11/2005 |
| CN | 1703279 A | 11/2005 |
| CN | 2904674 | 5/2007 |
| CN | 200966824 Y | 10/2007 |
| CN | 101115901 A | 1/2008 |
| CN | 201023852 | 2/2008 |
| CN | 201238609 | 5/2009 |
| CN | 201240612 Y | 5/2009 |
| CN | 201375023 | 1/2010 |
| CN | 101648041 A | 2/2010 |
| CN | 201430913 Y | 3/2010 |
| CN | 201592850 | 9/2010 |
| CN | 101878958 | 11/2010 |
| CN | 201657770 U | 12/2010 |
| CN | 102014677 A | 4/2011 |
| CN | 201830900 U | 5/2011 |
| CN | 201860753 U | 6/2011 |
| CN | 102264249 A | 11/2011 |
| CN | 102264420 A | 11/2011 |
| CN | 202122096 | 1/2012 |
| CN | 202172846 | 3/2012 |
| CN | 102655773 A | 9/2012 |
| CN | 202722498 | 2/2013 |
| CN | 202750708 | 2/2013 |
| CN | 103052380 A | 4/2013 |
| CN | 103960782 A | 8/2014 |
| CN | 203986095 U | 12/2014 |
| CN | 204048047 U | 12/2014 |
| CN | 104602553 A | 5/2015 |
| CN | 204317492 U | 5/2015 |
| CN | 104684422 A | 6/2015 |
| CN | 104983079 A | 10/2015 |
| CN | 105310114 A | 2/2016 |
| CN | 105394816 A | 3/2016 |
| CN | 106102863 A | 11/2016 |
| DE | 594585 | 3/1934 |
| DE | 1950439 | 4/1971 |
| DE | 2940797 | 4/1981 |
| DE | 3148335 | 7/1983 |
| DE | 3218760 | 12/1983 |
| DE | 3936687 | 5/1992 |
| DE | 29719509 U1 | 1/1998 |
| DE | 19630619 | 2/1998 |
| DE | 19654945 | 3/1998 |
| DE | 10330681 | 6/2004 |
| DE | 202006013439 | 10/2006 |
| DE | 202013100606 | 2/2013 |
| EA | 019736 B1 | 5/2014 |
| EA | 022685 B1 | 2/2016 |
| EP | 280262 | 8/1988 |
| EP | 0358002 A2 | 3/1990 |
| EP | 0358114 | 3/1990 |
| EP | 0444553 | 9/1991 |
| EP | 04888488 A1 | 6/1992 |
| EP | 0845220 | 6/1998 |
| EP | 0847220 A2 | 6/1998 |
| EP | 0295122 | 12/1998 |
| EP | 0893071 | 1/1999 |
| EP | 0893171 A1 | 1/1999 |
| EP | 1166814 | 1/2002 |
| EP | 1166847 | 1/2002 |
| EP | 1468618 A1 | 10/2004 |
| EP | 1736065 | 12/2006 |
| EP | 1757921 A2 | 2/2007 |
| EP | 1820748 A1 | 8/2007 |
| EP | 1847671 | 10/2007 |
| EP | 1950439 A1 | 7/2008 |
| EP | 2018886 | 1/2009 |
| EP | 2022349 | 2/2009 |

(56) References Cited

FOREIGN PATENT DOCUMENTS

| | | |
|---|---|---|
| EP | 2113178 | 11/2009 |
| EP | 2340729 A1 | 7/2011 |
| EP | 2358418 A1 | 8/2011 |
| EP | 2698070 | 2/2014 |
| EP | 2907397 | 4/2014 |
| EP | 2762019 | 8/2014 |
| EP | 2785208 A1 | 10/2014 |
| EP | 2801273 A2 | 11/2014 |
| EP | 2835062 | 2/2015 |
| EP | 2907397 B1 | 9/2017 |
| EP | 3117860 B1 | 1/2019 |
| FR | 472030 | 11/1914 |
| FR | 960469 | 4/1950 |
| FR | 1292446 | 5/1962 |
| GB | 30472 | 12/1909 |
| GB | 191100628 | 11/1911 |
| GB | 25575 | 3/1912 |
| GB | 191311086 | 9/1913 |
| GB | 110216 | 10/1917 |
| GB | 111454 | 11/1917 |
| GB | 120016 | 10/1918 |
| GB | 160493 | 3/1921 |
| GB | 163124 | 5/1921 |
| GB | 215992 | 5/1924 |
| GB | 268967 | 4/1927 |
| GB | 402064 | 11/1933 |
| GB | 507955 | 6/1939 |
| GB | 544329 | 4/1942 |
| GB | 565574 | 11/1944 |
| GB | 611596 | 11/1948 |
| GB | 626888 | 7/1949 |
| GB | 871869 | 7/1961 |
| GB | 1313525 | 4/1973 |
| GB | 1046183 | 7/1988 |
| GB | 2275464 | 8/1994 |
| GB | 2068034 | 11/1997 |
| GB | 2369108 | 5/2002 |
| GB | 4000273 | 12/2006 |
| GB | 4006615 | 10/2008 |
| GB | 2504075 A | 1/2014 |
| GB | 220229 | 8/2014 |
| HK | 1196511 | 12/2014 |
| HK | 1226611 | 10/2017 |
| JP | S5289386 A | 7/1977 |
| JP | S57-052456 | 3/1982 |
| JP | 57S-140354 U | 8/1982 |
| JP | S59-106340 | 1/1986 |
| JP | 61-096765 | 5/1986 |
| JP | S61-096763 | 5/1986 |
| JP | 61-096765 | 1/1988 |
| JP | H1117775 A | 5/1989 |
| JP | 2124081 | 5/1990 |
| JP | H02124082 A | 5/1990 |
| JP | H05-309136 | 11/1993 |
| JP | H6-315366 A | 11/1994 |
| JP | H07147965 A | 6/1995 |
| JP | H08-299862 | 11/1996 |
| JP | H08511176 A | 11/1996 |
| JP | 11089551 | 4/1999 |
| JP | H11503912 A | 4/1999 |
| JP | H11514081 A | 11/1999 |
| JP | 2001502542 A | 2/2001 |
| JP | 2002527153 A | 8/2002 |
| JP | 3093201 U | 4/2003 |
| JP | 2004332069 | 11/2004 |
| JP | 2005-013092 | 1/2005 |
| JP | 2005-138773 | 6/2005 |
| JP | 2005524067 A | 8/2005 |
| JP | 2005537918 A | 12/2005 |
| JP | 2005537919 A | 12/2005 |
| JP | 2005538149 A | 12/2005 |
| JP | 2005538159 A | 12/2005 |
| JP | 2007512880 A | 5/2007 |
| JP | 2007-297124 | 11/2007 |
| JP | 2009509523 A | 3/2009 |
| JP | 2009-526714 | 7/2009 |
| JP | 2009537119 A | 10/2009 |
| JP | 2011-087569 | 5/2011 |
| JP | 2011515093 A | 5/2011 |
| JP | 2011518567 A | 6/2011 |
| JP | 2012506263 A | 3/2012 |
| JP | 2012-249854 | 12/2012 |
| JP | 2014524313 A | 9/2014 |
| JP | 2015513970 A | 5/2015 |
| KR | 20050037919 A | 4/2005 |
| KR | 20130006714 U | 11/2013 |
| NL | 6617184 | 6/1967 |
| RU | 2311859 C2 | 12/2007 |
| RU | 2336001 C2 | 10/2008 |
| RU | 2360583 C1 | 7/2009 |
| RU | 89927 U1 | 12/2009 |
| RU | 94815 U1 | 6/2010 |
| RU | 103281 U1 | 4/2011 |
| RU | 115629 U1 | 5/2012 |
| RU | 121706 | 11/2012 |
| RU | 122000 U1 | 11/2012 |
| RU | 124120 | 1/2013 |
| RU | 132318 U1 | 9/2013 |
| RU | 2509516 C2 | 3/2014 |
| UA | 78167 | 3/2013 |
| WO | WO9527412 | 10/1995 |
| WO | WO9632854 | 10/1996 |
| WO | WO9748293 A1 | 12/1997 |
| WO | WO-9817131 A1 | 4/1998 |
| WO | WO200009188 | 2/2000 |
| WO | WO200021598 | 4/2000 |
| WO | WO-0050111 A1 | 8/2000 |
| WO | WO-02051468 A2 | 7/2002 |
| WO | WO2002058747 | 8/2002 |
| WO | WO2002058747 A1 | 8/2002 |
| WO | WO2002060769 | 8/2002 |
| WO | WO2003028409 A1 | 4/2003 |
| WO | WO 2003/050405 A1 | 6/2003 |
| WO | WO2003083283 | 10/2003 |
| WO | WO2003083283 A1 | 10/2003 |
| WO | WO 2003/101454 | 12/2003 |
| WO | WO2004/022128 | 3/2004 |
| WO | WO 2004/022242 A1 | 3/2004 |
| WO | WO2004022242 | 3/2004 |
| WO | WO2004022243 | 3/2004 |
| WO | WO2005106350 | 11/2005 |
| WO | WO 2005106350 A2 | 11/2005 |
| WO | WO2006082571 | 8/2006 |
| WO | WO 2007/042941 | 4/2007 |
| WO | WO 2007040941 A2 | 4/2007 |
| WO | WO 2007/131449 A | 11/2007 |
| WO | WO-2007131448 A1 | 11/2007 |
| WO | WO-2007141668 A2 | 12/2007 |
| WO | WO2008006048 | 1/2008 |
| WO | WO-2008038144 A2 | 4/2008 |
| WO | WO2008104870 | 9/2008 |
| WO | WO2009015410 | 2/2009 |
| WO | WO2009/092419 | 9/2009 |
| WO | WO2009118085 A1 | 10/2009 |
| WO | WO 2009132793 A1 | 11/2009 |
| WO | WO2010045670 A1 | 4/2010 |
| WO | WO2010045671 A1 | 4/2010 |
| WO | WO 2011/050943 A1 | 5/2011 |
| WO | WO 2011109849 A1 | 9/2011 |
| WO | WO 2011137453 A2 | 11/2011 |
| WO | WO 2012025496 A1 | 3/2012 |
| WO | WO 2012/065310 A1 | 5/2012 |
| WO | WO2012065754 | 5/2012 |
| WO | WO-2012106739 A1 | 8/2012 |
| WO | WO2012114082 | 8/2012 |
| WO | WO 2013034453 A1 | 3/2013 |
| WO | WO 2013034460 A1 | 3/2013 |
| WO | WO2013045942 | 4/2013 |
| WO | WO 2013057185 A1 | 4/2013 |
| WO | WO 2013/082173 | 6/2013 |
| WO | WO 2013098395 A1 | 7/2013 |
| WO | WO2013116558 | 8/2013 |
| WO | WO-2013116572 A1 | 8/2013 |
| WO | WO2014130695 | 8/2013 |

(56) References Cited

FOREIGN PATENT DOCUMENTS

| WO | WO2013142671 | 9/2013 |
|---|---|---|
| WO | WO2013152873 A1 | 10/2013 |
| WO | WO2013189050 | 12/2013 |
| WO | WO2013189052 | 12/2013 |
| WO | WO2014005275 | 1/2014 |
| WO | WO-2014012906 A1 | 1/2014 |
| WO | WO2014015463 | 1/2014 |
| WO | WO2014061477 A1 | 4/2014 |
| WO | WO 2014140320 A1 | 9/2014 |
| WO | WO 2014150131 A1 | 9/2014 |
| WO | WO 2013/082173 | 10/2014 |
| WO | WO-2015114328 A1 | 8/2015 |
| WO | WO-2015165812 A1 | 11/2015 |

OTHER PUBLICATIONS

Application and File History for U.S. Appl. No. 14/888,514, filed Nov. 2, 2015, inventor Reevell.
Application and File History for U.S. Appl. No. 14/888,517, filed Nov. 2, 2015, Inventor Reevell.
Application and File History for U.S. Appl. No. 15/997,113, filed Jun. 4, 2018, inventor Buchberger.
Application and File History for U.S. Appl. No. 16/096,554, filed Oct. 25, 2018, Inventor Fraser.
Company Filtrona Richmond Inc., http://www.filtronaporoustechnologies.com, Nov. 19, 2018, 1 page.
Decision on Appeal, U.S. Appl. No. 14/306,831, dated Mar. 26, 2020, 6 pages.
Examination Report dated Nov. 20 For Australian Application No. 2017256084, 3 pages.
Extended European Search Report for Application No. 18205608.5, dated Jul. 12, 2019, 7 pages.
Extended European Search Report for Application No. EP17197150.5, dated Mar. 1, 2018, 6 pages.
Extended European Search Report for Application No. 16151458.3, dated Jul. 11, 2016, 8 pages.
Extended European Search Report for European Application No. 15178588, dated Apr. 22, 2016, 4 pages.
International Preliminary Report on Patentability for Application No. PCT/AT2009/000413, dated May 5, 2011, 7 pages.
International Preliminary Report on Patentability for Application No. PCT/AT2009/000414, dated Apr. 26, 2011, 7 pages.
International Preliminary Report on Patentability for Application No. PCT/EP2012/003103, dated Feb. 6, 2014, 7 pages.
International Preliminary Report on Patentability for Application No. PCT/GB2017/051139, dated Aug. 6, 2018, 7 pages.
International Search Report and Written Opinion for Application No. PCT/GB2017/051139, dated Aug. 9, 2017, 14 pages.
Notice of Opposition dated Oct. 30, 2019 for European Application No. 16166656.5, 39 pages.
Notification to Grant Patent Right for Invention dated Oct. 25, 2018 for Chinese Application No. 201610086101.4, 2 pages.
Office Action and Search Report dated Feb. 28, 2019 for Japanese Application No. 2018-088088, 25 pages.
Office Action dated Jul. 2, 2020 for Chinese Application No. 201780020023.0 filed Sep. 25, 2018, 22 pages.
Office Action for European Application No. 16166656, dated Jul. 29, 2020, 7 pages.
Office Action for Chilean Application No. 201701486 dated Nov. 11 2019, 10 pages.
Office Action dated Mar. 16, 2020 for Chinese Patent Application No. 201610255788.X, filed Oct. 21, 2009, 21 pages.
Office Action dated Jan. 25, 2019 for European Application No. 17189951.1, 4 pages.
Office Action dated Sep. 27, 2019 for Korean Application No. 10-20197005785, 13 pages.
Office Action dated May 4, 2018 for Chinese Application No. 201610086101.4, 7 pages.
Search Report for Chilean Application No. 2019-11665, dated Nov. 11, 2019, 10 pages.
Search Report for Japanese Application No. 2016134648, dated Mar. 28, 2017, 29 pages.
Search Report for Japanese Application No. 2011532464, dated Sep. 24, 2013, 53 pages.
Search Report dated Apr. 14, 2017 for Japanese Application No. 2016-134648, 31 pages.
Search Report dated Sep. 19, 2013 for Japanese Application No. 2011-532464, 116 pages.
Search Report dated Jun. 24, 2019 for Russian Application No. 2018137583, 2 pages.
Search Report dated Apr. 25, 2018 for Chinese Application No. 201610086101.4, 1 page.
Search Report dated Apr. 29, 2019 for Russian Application No. 2018137501, 12 pages.
Written Opinion for Application No. PCT/AT2009/000413, dated Jan. 25, 2010, 5 pages.
Written Opinion for Application No. PCT/AT2009/000414, dated Jan. 26, 2010, 14 pages.
Written Opinion for Application No. PCT/AT2012/000017, dated Jul. 3, 2012, 4 pages.
International Preliminary Report on Patentability for International Application No. PCT/GB2014/051688 dated Dec. 8, 2015.
International Search Report or International Application No. PCT/GB2014/051688 dated Aug. 26, 2014.
Written Opinion for International Application No. PCT/GB2014/051688 dated Aug. 26, 2014.
International Search Report of the International Searching Authority for International Application No. PCT/GB2014/051633 dated Dec. 4, 2014.
Written Opinion of the International Searching Authority for International Application No. PCT/GB2014/051633 dated Dec. 4, 2014.
Notification of Transmittal of IPRP for International Application No. PCT/GB2014/051633 dated Oct. 23, 2015.
Office Action dated Sep. 3, 2014, for Russian Application No. 2013504605.
Russian Decision to Grant, Application No. 2015146845, dated Apr. 27, 2017, 8 pages.
International Preliminary Report on Patentability dated Aug. 13, 2013 for International Application No. PCT/AT2012/000017.
Great Britain Examination Report, Application No. GB1405720.2, dated Jun. 27, 2017, 3 pages.
GB Intention to Grant, Application No. GB1405720.2, dated Sep. 26, 2017, 2 pages.
Russian Office Action, Application No. 2015146847, dated Sep. 22, 2017, 11 pages.
Decision to Grant in Russian Application No. 120267, dated Oct. 26, 2016. No English translation available.
Translation of Search Report for JP2016517671 dated Feb. 1, 2017.
Chinese Office Action for Chinese Application No. 201480031296.1 dated Mar. 27, 2017.
Chinese Notification of First Office Action for Chinese Application No. 2014800319265 dated Apr. 21, 2017.
Korean Office Action, Korean Application No. 10-2015-7034538, dated May 12, 2017, 5 pages.
Hong Kong Publication, Application No. 16113324.2, published Oct. 6, 2017, 1 page.
Hong Kong Publication, Application No. 14110165.2, published Dec. 19, 2014, 1 page.
Russian Office Action, Application No. 2016142584, dated Nov. 21, 2017, 6 pages (8 pages with translation).
Decision to Grant, Russian Application No. 2011120430, dated Apr. 1, 2014, 10 pages.
Japanese Search Report, Application No. 2016-134648, dated Mar. 28, 2017, 11 pages.
Japanese Search Report, Application No. 2014-179732, dated Aug. 25, 2015, 5 pages.
International Preliminary Report on Patentability for corresponding International Application No. PCT/GB2015/051213 dated Jul. 14, 2016.
International Search Report for corresponding International Application No. PCT/GB2015/051213 dated Jul. 16, 2015.

(56) References Cited

OTHER PUBLICATIONS

Written Opinion of the International Preliminary Examining Authority for International Application No. PCT/GB2015/051213 dated Mar. 29, 2016.
International Search Report and Written Opinion dated Feb. 6, 2013 for PCT/EP0212/070647 filed Oct. 18, 2012.
Chinese Office Action for Chinese Application No. 201480024978.X dated Jan. 18, 2017.
European Search Report for European Application No. 15178588 dated Apr. 14, 2016.
International Preliminary Report on Patentability, dated Apr. 22, 2014, for International Patent Application No. PCT/EP2012/070647, filed Oct 18, 2012.
International Search Report and Written Opinion for International Application No. PCT/EP2012/003103, dated Nov. 26, 2012.
Japanese Search Report, Application No. 2011-532464, dated Sep. 18, 2013, 73 pages.
Japanese Decision to Grant, application No. 2011-532464 dated Aug. 5, 2014, 3 pages.
International Search Report and Written Opinion for PCT/AT/2012/000017 dated Jul. 3, 2012.
International Search Report and Written Opinion for PCT/GB2014/051333 dated Jul. 17, 2014.
International Search Report and Written Opinion, International Application No. PCT/GB2014/051332 dated Jul. 21, 2014.
International Search Report and Written Opinion, International Application No. PCT/GB2014/051334 dated Jul. 21, 2014.
IPRP dated Aug. 5, 2015 for International Application No. PCT/GB2014/051333.
IPRP, International Application No. PCT/GB2014/051332 dated Nov. 12, 2015.
IPRP, International Application No. PCT/GB2014/051334 dated Nov. 12, 2015.
Japanese Notice of Reasons for Rejection for Japanese Application No. 2015-137361 dated May 31, 2016.
Russian Search Report for Russian Application No. 2015146843/12 (072088) dated Apr. 24, 2017.
Russian Office Action, Application No. 2014120213/12, dated Oct. 26, 2016, 7 pages.
Russian Office Action, Application No. 2014120213/12, dated Sep. 22, 2017, 11 pages.
Chinese Office Action, Application No. 201480024988.3, dated Dec. 30, 2016, 26 pages.
Chinese Office Action, Application No. 201480024988.3, dated Sep. 11, 2017, 21 pages.
European Extended Search Report, Application No. 17189951.1, dated Jan. 4, 2018, 8 pages (11 pages with translation).
Plasma polymerization (the company Diener electronic GmbH+Co. KG), www.plasma.de, retrieved on Oct. 17, 2017, 19 pages.
International Preliminary Report on Patentability (WIPO English Translation), dated Aug. 13, 2013 for International Patent Application No. PCT/AT2012/000017, filed Feb. 2, 2012.
Pulmonary Pharmacoloy: Delivery Devices and Medications, dated Sep. 6, 2017, 2 pages, available at www.cdeu.org/cecourses/z98207/ch4.htm.
Dunn P and Reay D, Heat Pipes, 4th edition, 1994, ISBN 0080419038, 14 pages.
Application and File History for U.S. Appl. No. 13/125,343, filed Apr. 21, 2011 inventor Buchberger.
Japanese Notice of Reasons for Rejection dated Sep. 8, 2015 for Japanese Application No. 2014179732.
Japanese Notice of Reasons for Rejection dated Oct. 15, 2013 for Japanese Application No. 2011532464.
Application and File History for U.S. Appl. No. 13/984,512, filed Aug. 29, 2013, inventor Buchberger.
Application and File History for U.S. Appl. No. 14/268,909, filed May 2, 2014, inventor Buchberger.
Application and File History for U.S. Appl. No. 14/306,831, filed Jun. 17, 2014, inventor Buchberger.
European Search Report for European Application No. 16166656 dated Oct. 11, 2016.
Notice of Opposition Letter from EPO. Opposition against: EP2358418 dated Mar. 1, 2017.
Rudolph G, BAT Cigarettenfabriken GmbH, 1987, The Influence of $CO_2$ on the Sensory Characteristics of the Favor-System, http://legacy.library.ucsf.edu/tid/sla51f00.
Application and File History for U.S. Appl. No. 15/470,078, filed Mar. 27, 2017, inventor Buchberger.
Application and File History for U.S. Appl. No. 15/470,089, filed Mar. 27, 2017, inventor Buchberger.
Japanese Notification of Reasons for Refusal for Japanese Application No. 2014179732 dated Sep. 3, 2015 and dated Sep. 8, 2015.
Japanese Notice of Reasons for Refusal, dated Oct. 7, 2013 and dated Oct. 15, 2013 for Japanese Application No. 2011532464.
International Search Report for International Application No. PCT/AT2009/000413 dated Jan. 25, 2010.
Translation of Chinese First Office Action for Chinese Application No. 200980152395.4 dated Dec. 3, 2012.
Translation of Chinese Second Office Action for Chinese Application No. 200980152395.4 dated Aug. 20, 2013.
Japanese Reasons for Rejection for Japanese Application No. 2016134648 dated May 23, 2017.
Application and File History for U.S. Appl. No. 14/353,256, filed Apr. 21, 2014, Inventor: Buchberger.
Japanese Decision to Grant, Application No. 2016-134648, dated May 22, 2018, 3 pages (4 pages with translation).
Japanese Office Action, Application No. 2016-564977, dated Dec. 5, 2017, 3 pages (6 pages with translation).
Japanese Search Report, Application No. 2016-864977, dated Oct. 25, 2017, 9 pages (19 pages with translation).
Chinese Office Action, Application No. 201580022356.8, dated Jul. 18, 2018, 8 pages (15 pages with translation).
International Search Report and Written Opinion for International Application No. PCT/AT2009/000414 dated Jan. 26, 2010.
Kynol, *Kynol Standard Specifications of Activated Carbon Fiber Products*, 2 pages, as retrieved on Sep. 19, 2013.
Application and File History for U.S. Appl. No. 14/296,2, filed Jun. 5, 2014 inventor Buchberger.
Application and File History for U.S. Appl. No. 15/454,156, filed Mar. 9, 2017, inventor Buchberger.
Application and File History for U.S. Appl. No. 15/307,095, filed Oct. 27, 2016, inventor Buchberger.
Chinese Office Action, Application No. 201610371843.1, dated Sep. 30, 2018, 6 pages (11 pages with translation).
Application and File History for U.S. Appl. No. 14/235,210, filed Mar. 4, 2014, Inventor: Buchberger.
Application and File History for U.S. Appl. No. 15/470,095, filed Mar. 27, 2017, Inventor: Buchberger.
Application and File History for U.S. Appl. No. 14/594,065, filed Jan. 9, 2015, Inventor: Buchberger.

\* cited by examiner

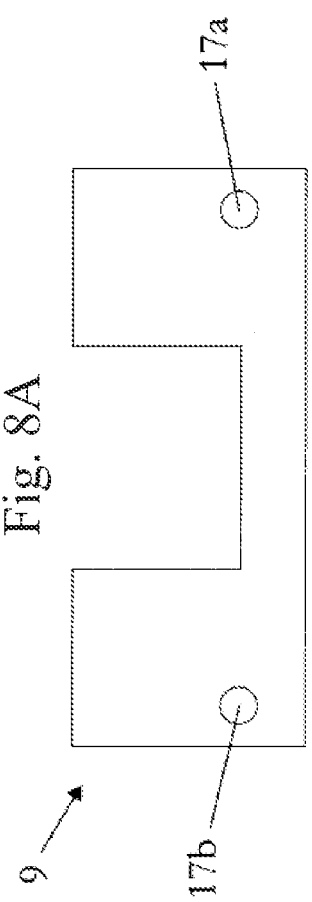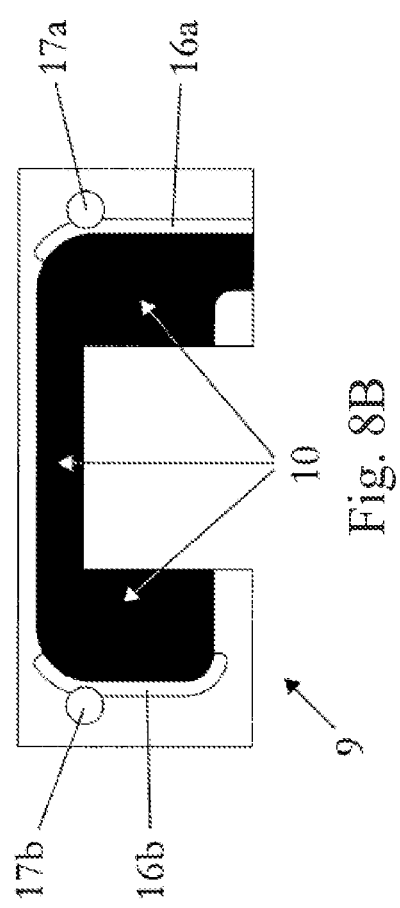

INHALER COMPONENT

RELATED APPLICATION

This application is a continuation of application Ser. No. 14/268,909 filed May 2, 2014, which in turn is a continuation of application Ser. No. 13/984,512, filed Aug. 29, 2013, now U.S. Pat. No. 8,752,545 issued Jun. 17, 2014, which is the National Stage of International Application No. PCT/AT2012/000017, filed Feb. 2, 2012, which in turn claims priority to Austrian Patent Application No. A187/2011, filed Feb. 11, 2011, and to Austrian Patent Application No. A1095/2011, filed Jul. 27, 2011, each of which is hereby fully incorporated herein by reference.

FIELD

The invention relates to an inhaler component for the formation of a vapor-air mixture or/and of a condensation aerosol by evaporating a liquid material and, if necessary, condensing the vapor formed, comprising: a heating element for the evaporation of a portion of the liquid material; a wick for the automatic supply of the heating element with the liquid material, the said wick having at least two end sections arranged at a distance from each other; a first capillary gap for the automatic supply of the wick with the liquid material, wherein a first end section of the wick extends into the first capillary gap.

BACKGROUND

Definition of terms: In the present patent application the term "inhaler" refers to medical as well as non-medical inhalers. The term refers furthermore to inhalers for the administration of drugs and materials which are not declared as drugs. The term refers, in addition, to smoking articles and cigarette substitutes, such as those in European patent class A24F47/00B, for example, as far as these are intended to supply the user with a vapor-air mixture or/and a condensation aerosol. The term "inhaler" also implies no restrictions on how the vapor-air mixture or/and condensation aerosol formed is supplied to the user or his body. The vapor-air mixture or/and condensation aerosol can be inhaled into the lungs or, in addition, only supplied to the oral cavity--without inhalation into the lungs.

"Capillary gap" means any gap which causes liquid transport solely on the basis of the capillary action of its confining walls. Wicks, wrapped wicks or channels filled with wick material are not capillary gaps.

WO 2010/045671 (Helmut Buchberger) describes an inhaler component for the intermittent, inhalation or pull-synchronous formation of a vapor-air mixture or/and condensation aerosol, consisting of (FIGS. 9 to 12 and FIGS. 17 to 18) a housing 3, a chamber 21 provided in the housing 3, an air intake opening 26 for the supply of air from the environment into the chamber 21 and an electric heating element for the evaporation of a portion of a liquid material 16, in which case the vapor formed mixes in the chamber 21 with the air supplied by the air intake opening 26 and the vapor-air mixture or/and condensation aerosol is or are formed. Furthermore, the inhaler component comprises a wick with a capillary structure, which wick forms with the heating element a laminar composite 22 and automatically resupplies the heating element with the liquid material 16 after evaporation. At least one heated section of the composite 22 is arranged without contact in the chamber 21 and the capillary structure of the wick lies exposed to a large extent in the said section at least on one side 24 of the laminar composite. One end of the laminar composite 22 projects into a capillary gap 41, which is coupled or is capable of being coupled by capillary to a liquid container 4 containing the liquid material 16. The capillary gap 41 draws the liquid material 16 from the liquid container 4 and conveys it to the wick.

After evaporation or inhalation the user of the inhaler component must observe a waiting period, during which the liquid material 16 can again completely infiltrate the wick. Evaporations before the expiration of the waiting period can lead to various disadvantageous consequences, for example a decrease in the given aerosol quantity or/and a local overheating of the wick, possibly associated with a decomposition of the liquid material and a degradation of the organoleptic characteristics of the vapor-air mixture or aerosol formed. In prototypes based on highly diluted ethanol or/and aqueous nicotine solutions, it was possible to obtain complete infiltration of the wick within 10 s. If the inhaler component is used as a cigarette replacement, then a waiting period of 10 s may be acceptable for many smokers; for some smokers, however, it may be too long. Furthermore, with the same prototypes it has been shown that even when the waiting period mentioned is adhered to, disturbances of the infiltration can occur. These disturbances rarely arise, but can lead to the same disadvantageous consequences as described above. The disturbances are characterized by an unsatisfactory wetting of the capillary structure of the wick by the liquid material and occur preferably locally, in regions of the wick which are peripheral in relation to the capillary gap.

SUMMARY

The object of the invention is to remedy the aforementioned disadvantages of the arrangement known from the state of the art. More particularly, it is the object of the invention to design an inhaler component of the type described in the preamble in such a way that the wick is infiltrated with the liquid material as rapidly as possible and no unpleasantly long waiting periods occur. Local disturbances of the infiltration are likewise to be avoided. All of this is to be achieved, if possible, without additional structural outlay. The production costs of the inhaler component should likewise not be increased.

This object is achieved by the characterizing features of claim 1. Accordingly, the inhaler component is provided with a second capillary gap, which holds the second end section of the wick. The wick is thus supplied with the liquid material from two sides. As a result, the waiting period for complete infiltration of the wick can be at least halved as compared with a conventional one-sided supply. If one considers that the infiltration of the wick with the liquid material takes place in a degressive-proportional manner, i.e. comparatively rapidly at the beginning and then more slowly, then it becomes clear that the waiting period for the complete infiltration of the wick by the arrangement according to the invention can be shortened by significantly more than 50%. Similarly advantageous effects result regarding the security of supply of the wick: the particularly endangered regions of the wick on the periphery in relation to the first capillary gap can now be reliably supplied with the liquid material over a short distance from the second capillary gap.

In a preferred embodiment of the invention it is provided that the first and second capillary gaps are connected to each other by a third capillary gap. The first and second capillary gaps thus communicate with each other via the third capillary gap. Thus any uneven supply of the first and second capillary gap with the liquid material can be equalized, and the security of supply to the wick further improved.

It is further provided according to the invention that one of the capillary gaps is coupled or capable of being coupled by capillary to a liquid container containing the liquid material. This capillary gap can for example be the first capillary gap. In this case the second capillary gap would be supplied with the liquid material exclusively via the third capillary gap. In addition, it could alternatively be provided that the third capillary gap is coupled or capable of being coupled by capillary to the liquid container. In this case the first and second capillary gaps would be supplied with the liquid material via the third capillary gap.

Conditions which are particularly simple structurally result if all the capillary gaps are situated in a common plane. A further structural simplification is obtained by all the capillary gaps being formed by a board, preferably a printed circuit board, and an upper section mounted on the board. In this case only two components are required to form all the capillary gaps.

In a first variant of embodiment the upper section has, according to the invention, a recess facing the board. The recess forms the capillary gaps in co-operation with the surface of the board, the depth of the recess setting the width of the capillary gaps. It is particularly advantageous for the recess to be bounded at least locally by one or more ventilation grooves. The ventilation grooves have the advantageous effect that the liquid material stored in the capillary gaps can be used more effectively as buffer volumes.

In a second alternative variant of embodiment the upper section is mounted on the end sections of the wick. The end sections of the wick act in this case as spacers which set the width of the capillary gaps. In this alternative variant of embodiment too, the upper section would be considered as being "mounted on the board", even if the two components do not touch each other directly.

The board is preferably designed in the form of a printed circuit board and it serves as such for supplying electrical energy to the—in this case—electric heating element. In this case it is particularly advantageous for the printed circuit board to be designed in the form of a multiple-layer, so-called multilayer, printed circuit board. As a result, the conductive strips supplying the electric current can in this case be concentrated in layers which do not affect the capillary gaps. In addition, more complex arrangements of conductive strips can also be implemented by means of multilayer printed circuit boards, a circumstance which proves advantageous at the latest when a plurality of electric heating elements are provided, and the heating elements are to be actuated independently of one another. Finally, on account of the multiple-layer arrangement of their conductive strips, multilayer printed circuit boards allow comparatively high electric currents to be transmitted.

In a further arrangement of the invention it is provided that the first capillary gap is coupled or is capable of being coupled to a first liquid container containing the liquid material and the second capillary gap is coupled or is capable of being coupled to a second liquid container containing the liquid material. By providing two liquid containers essentially independent of each other the security of supply of the wick with the liquid material can once again be increased.

Expedient and advantageous embodiments of the invention are illustrated in the drawings and are explained in greater detail in the following description.

BRIEF DESCRIPTION OF THE DRAWINGS

In the drawings:

FIG. 8A shows a view of the upper section forming the capillary gaps;

FIG. 8B shows a further view of the upper section forming the capillary gaps, with the capillary gaps and recess visible;

DETAILED DESCRIPTION

Figure 1:
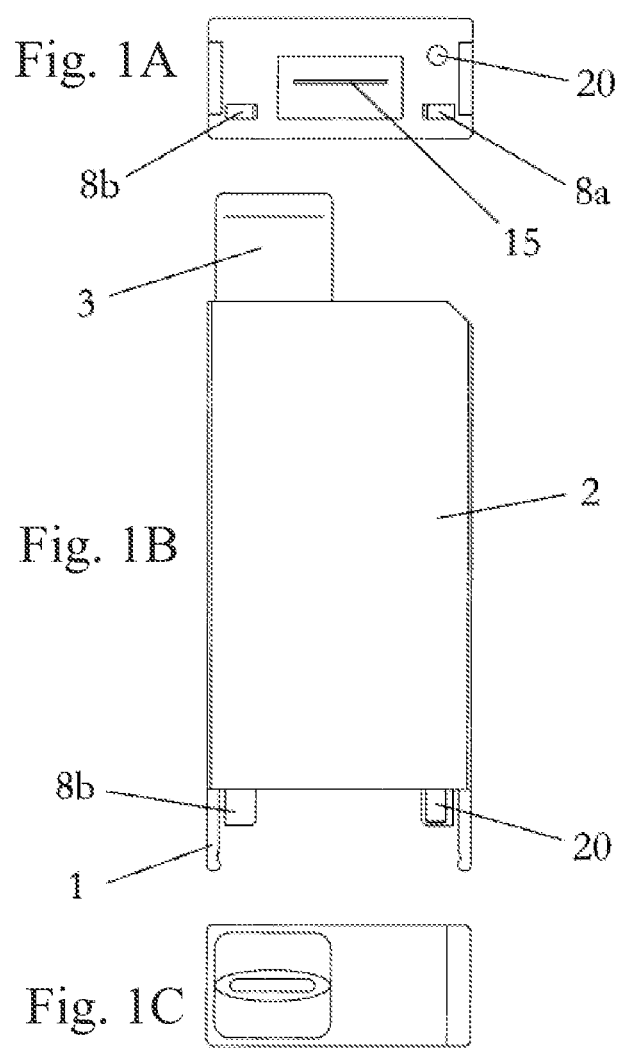
FIG. 1A shows a bottom view of an exemplary inhaler component according to the invention.
FIG. 1B shows a front view of an exemplary inhaler component according to the invention.
FIG. 1C shows a top view of an exemplary inhaler component according to the invention.

FIGS. 1A through 1C show multiple views of a first embodiment of an inhaler component according to the invention. The inhaler component in the specific example is designed in the form of an interchangeable part of the inhaler and is capable of being coupled via a snap connection 1 to a reusable inhaler part (not further shown). The inhaler component together with the reusable inhaler part forms the inhaler. The inhaler component consists of a housing 2 and further comprises a mouthpiece 3, by way of which the user of the inhaler draws the vapor-air mixture or/and the condensation aerosol.

FIGS. 2 to 5 provide further information about the internal structure of the inhaler component. Thus a carrier plate 4, which is preferably designed as a printed circuit board, is located in the housing 2. The printed circuit board 4 carries a laminar composite 5. The laminar composite 5 consists of a wick 7 and an electric heating element 6, which are connected to each other in a laminar manner or integrated one into the other. The laminar composite 5 can be formed for example by a metal foil with metal fabric layers sintered on it. The laminar composite 5 can alternatively also consist of an open-pored metal foam. The open-pored capillary structure of the fabric layers sintered onto the metal foil or the metal foam forms the wick 7 and the electrical resistance of the metal forms the heating element 6. Suitable metallic resistance materials are, for example, high-grade steels such as AISI 304 or AISI 316 as well as heat-conducting alloys, in particular NiCr alloys.

The wick 7 and the laminar composite 5 containing it have two end sections 7a and 7b arranged at a distance from each other. The laminar composite 5 is mounted with these end sections on the printed circuit board 4. The laminar composite 5 is furthermore electrically contacted in the region of the end sections 7a and 7b on conductive strips of the printed circuit board 4. The electrical contacting of the laminar composite 5 or the resistance heating element 6 thereof mat, for example, consist of an adhesive joint by means of an electrically conducting adhesive, for example, by means of a silver-containing adhesive based on epoxide. The printed circuit board 4 projects from the outside surface of the housing 2 in the form of two plug contacts 8a and 8b. The two plug contacts 8a and 8b serve to introduce the electrical energy into the inhaler component. The electrical energy is supplied to the electrical resistance heating element 6 via conductive strips of the printed circuit board 4. The printed circuit board 4 is preferably designed in the form of a multiple-layer, so-called multilayer, printed circuit board. The conductive strips are thus present in several layers. The advantages of this special type of printed circuit board have already been described above. The electrical energy is preferably drawn from the reusable inhaler part. For this purpose the reusable inhaler part contains a battery and an electrical control circuit for controlling the energy supply.

An upper section 9 having a recess or depression 10 is placed flat on the printed circuit board 4—see FIGS. 3 to 8B. The recess 10 is shown as a black area in FIG. 8B and has a depth of typically 0.2 mm. The recess 19 faces the printed circuit board 4 and, in conjunction with the surface thereof, forms a capillary gap. The capillary gap is shown diagrammatically in FIG. 2 as a black area and consists of three sections: a first capillary gap 11a, into which the laminar composite 5 or wick 7 with its end section 7a projects; a second capillary gap 11b, into which the laminar composite 5 or wick 7 with its end section 7b projects; and a third capillary gap 11c, which connects the first capillary gap 11a to the second capillary gap 11b. The first capillary gap 11a is connected to the liquid container 12 formed by the housing 2 or arranged in it. The liquid container 12 stores a liquid material 13. The capillary forces in the capillary gap 11a pull the liquid material 13 from the liquid container 12 into the capillary gap 11a. The liquid material 13 first reaches the end section 7a of the laminar composite 5.

There the liquid material 13 moistens the capillary structure of the wick 7, after which the wick 7 can be further infiltrated from this side with liquid material 13. In parallel with this the liquid material 13 flows into the capillary gap 11c and finally arrives by way of the latter at the capillary gap 11b, where in the end section 7b it again moistens the capillary structure of the laminar composite 5 or the wick 7. The wick 7 is thus infiltrated from two sides with the liquid material 13. Since the flow resistance of the capillary gaps is substantially lower than the flow resistance of the wick 7, the infiltration of the wick 7 takes place at almost the same time or symmetrically on both sides. Compared with arrangements with only one-sided supply of the wick 7 (see WO 2010/045671) the infiltration time can be substantially reduced.

After the wick 7 or laminar composite 5 has been completely infiltrated with the liquid material 13, the electrical energy can be supplied to the electrical resistance heating element 6 by way of the conductive strips of the printed circuit board 4 and the liquid material 13 evaporated. TO ensure as far as possible that the conductive strips do not affect the capillary gaps, it is advantageous if the conductive strips are arranged primarily on the back of the printed circuit board 4 and, if necessary, in intermediate layers (multilayer printed circuit board), and the individual conductive strips interconnected appropriately according to the state of the art by means of so-called plated-through holes. The vapor released is mixed in a chamber 14 provided in the housing 2 with the air supplied from the environment through an air intake opening 15 (see FIGS. 3 to 5) and forms the vapor-air mixture or/and condensation aerosol, which can then be transferred to a user via the mouthpiece 3.

Figure 2:
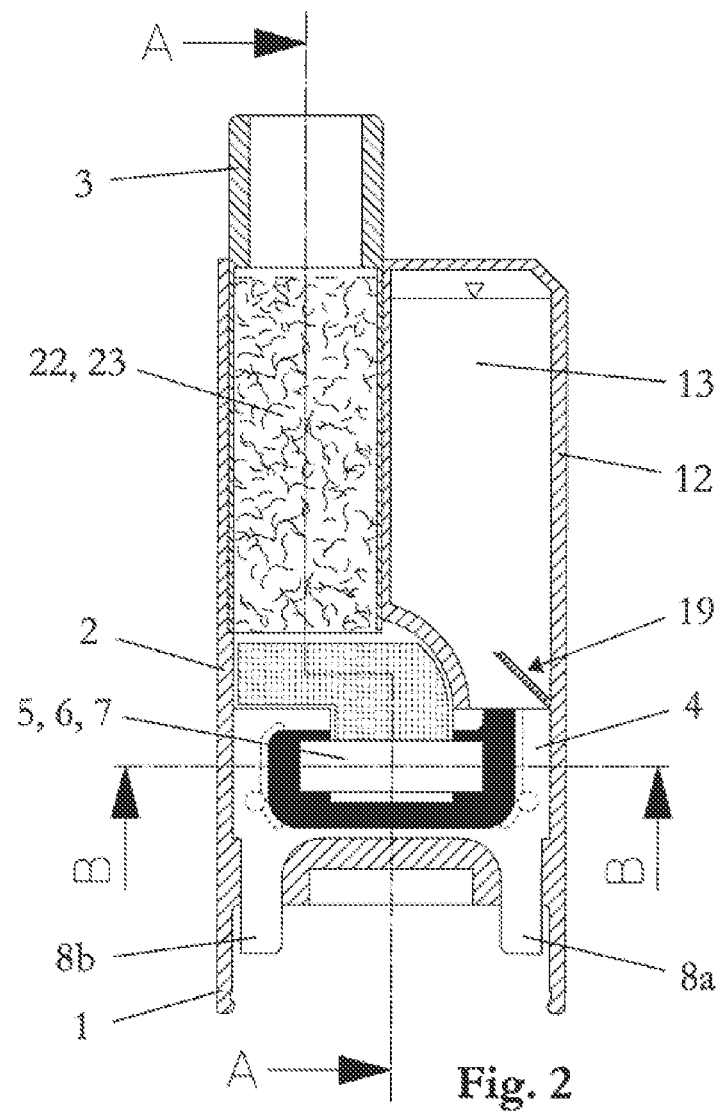
FIG. 2 is a longitudinal section through the inhaler component according to FIG. 1B at the level of the laminar composite.
Figure 4:
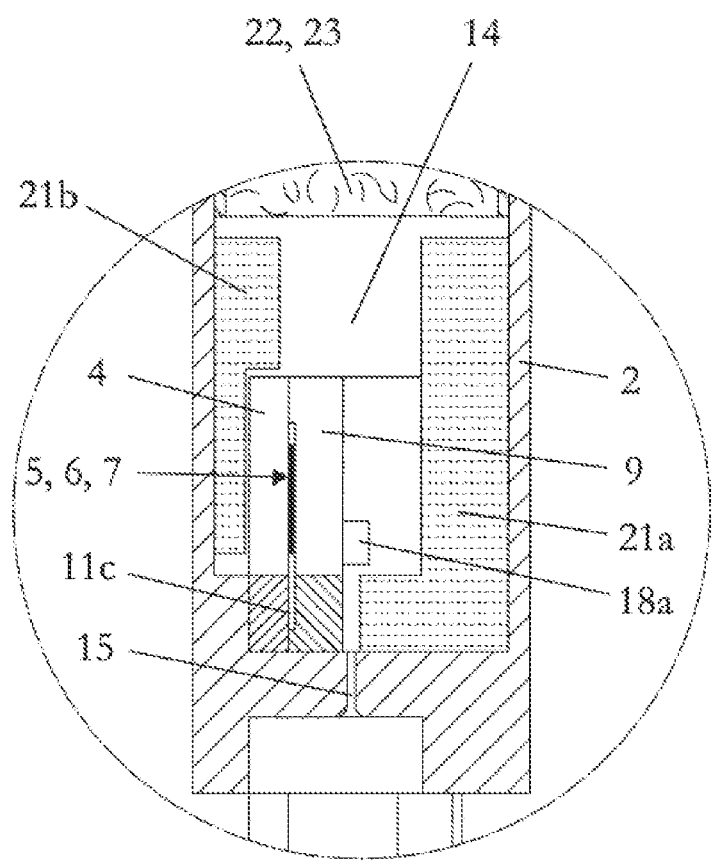
FIG. 4 shows the detail from FIG. 3 in an enlarged view.
Figure 5:
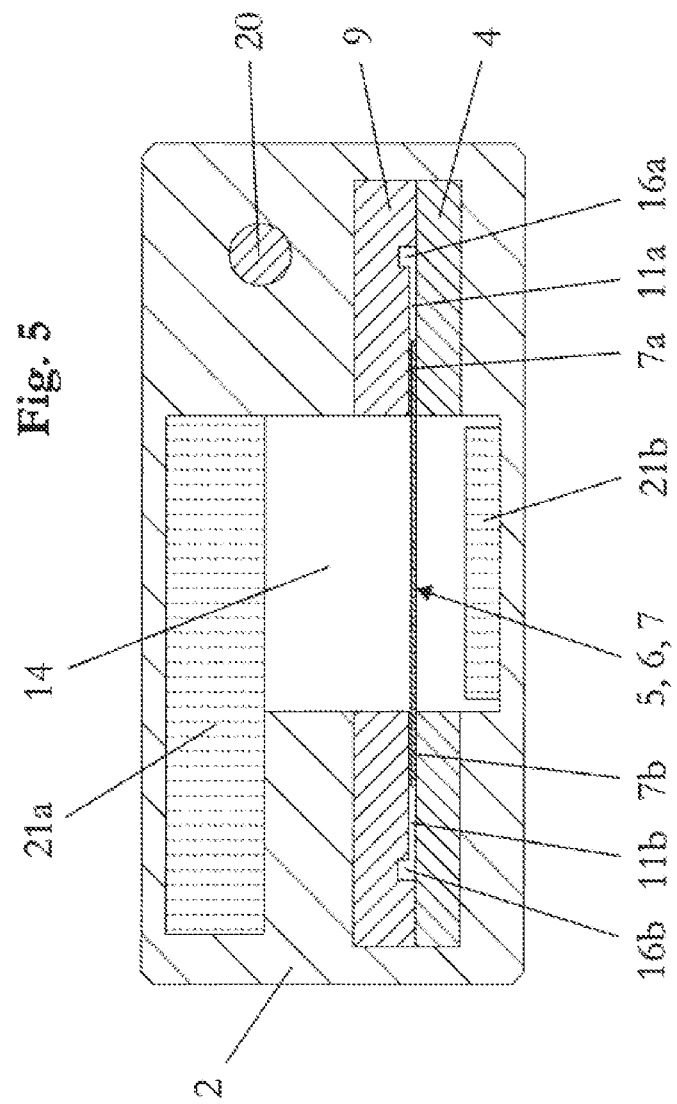
FIG. 5 is a cutaway view of the inhaler component along the line B-B in FIG. 2.
Figure 6:
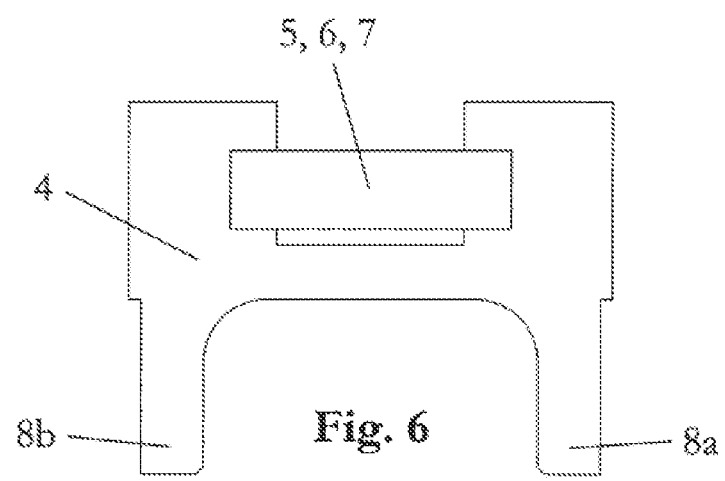
FIG. 6 shows the printed circuit board including a laminar composite.
Figure 7:
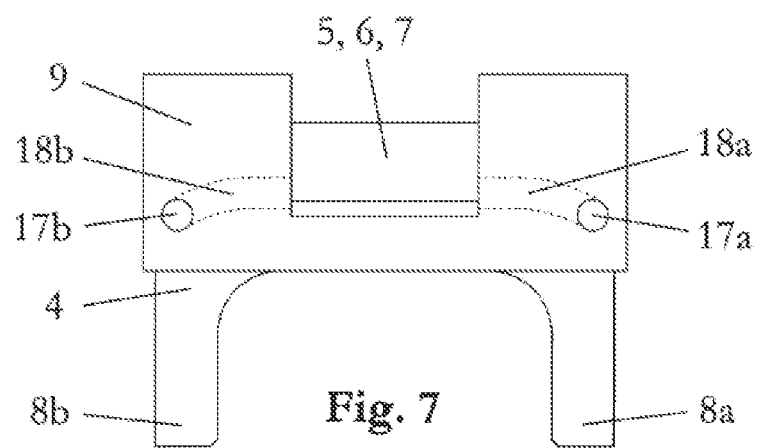
FIG. 7 shows the printed circuit board including a laminar composite joined to the upper section forming the capillary gaps.

In accordance with FIGS. 8A and 8B, the recess 10 in the upper section 9 is bounded in the region of the first capillary gap 11a by a first ventilation groove 16a and in the region of the second capillary gap 11b by a second ventilation groove 16b. In FIG. 2 the ventilation grooves 16a and 16b are represented diagrammatically as broken lines and in FIG. 5 are shown in cross-section. The ventilation groove 16a extends up to the liquid container 12 and ensures that each volume of liquid material 13 removed from the liquid container is replaced by an equivalent volume of air. The ventilation slots 16a and 16b draw in the air via ventilation holes 17a and 17b which are formed by the upper section 9 and which for their part are connected to the chamber 14 via connecting channels 18a and 18b formed by the housing 2. The connecting channels 18a and 18b are shown diagrammatically in FIG. 7 as broken lines. The outlet of the connecting channel 18a into the chamber 14 is shown in FIG. 4.

In principle, all known printed circuit board materials are suitable as the material for the printed circuit board 4, in particular the material types FR1 to FR5. The upper section 9 is added to the printed circuit board 4 by adhesive bonding and likewise consists preferably of a plastic. It is important that the surfaces of the printed circuit board 4 as well as of the upper section 9 are well moistened by the liquid material 13. It is preferable for highly diluted ethanol or/and aqueous solutions to be used as the liquid material 13, in which the actual active substances, aerosol-forming materials, flavorings, as well as, if necessary, further ancillary materials are dissolved or/and emulsified. The wettability as well as the adhesion of the plastics can be substantially improved by surface activation, for example by hydrophilization by means of plasma polymerization (the company Diener electronic GmbH+Co. KG, www.plasma.de).

Figure 9:
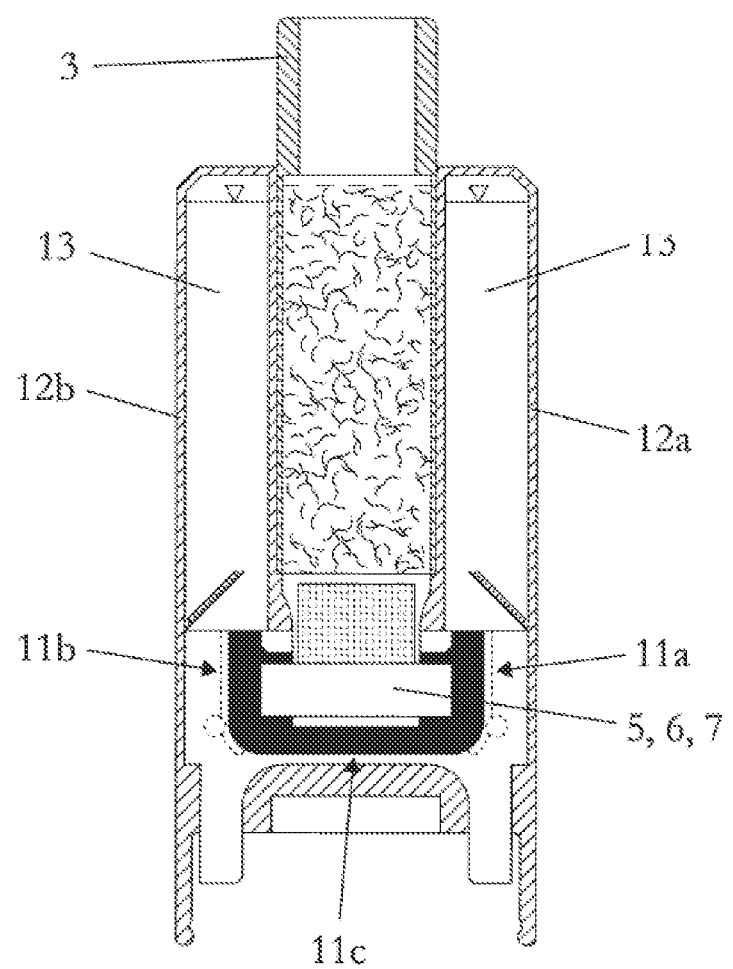
FIG. 9 shows an inhaler component according to the invention in an alternative embodiment in a view similar to FIG. 2.

FIG. 9 shows an alternative embodiment of the inhaler component according to the invention. This embodiment differs from the arrangement according to FIG. 2 essentially in that a second liquid container 12b containing the liquid material 13 is provided, which is coupled or is capable of being coupled to the second capillary gap 11b. If a disturbance of the liquid supply occurs in the first supply path (liquid container 12a and capillary gap 11a), then the laminar composite 5 or the wick 7 thereof can still be adequately supplied with liquid material 13 via the second supply path (liquid container 12b, capillary gap 11b and, if necessary, capillary gap 11c).

Figure 3:
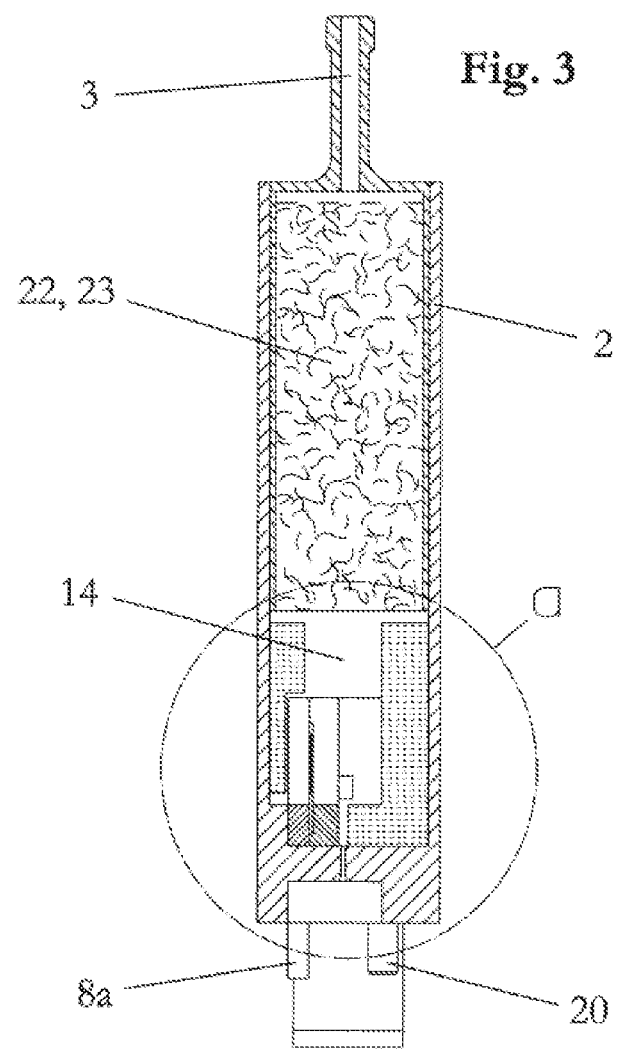
FIG. 3 is a cutaway view of the inhaler component along the line A-A in FIG. 2.

Still further components of the inhaler component are briefly described below. Even if these components are not directly relevant to the invention, their description nevertheless contributes to a better understanding of the function of the inhaler component according to the invention as a whole and ensures the workability of the invention still more certainly: as shown in FIG. 2, for example, the liquid container 12 has a valve-like, openable catch 19 on a front face. The openable catch 19 seals the liquid container 12 hermetically off from the exterior in its closed position. Only after opening the openable catch 19 can the liquid material 13 moisten the capillary gap 11a and then, through the action of capillary forces in the capillary gap, penetrate further to the laminar composite 5 and finally infiltrate the wick 7 of the laminar composite 5. The openable catch 19 is opened with the aid of a pin 20 mounted in the housing 2 in an axially adjustable manner (FIG. 3 and FIG. 5). A first end of the pin 20 is directed towards the openable catch 19. A second end extends from the outer surface of the housing 2 like an extension with the catch 19 still closed. The second end of the pin 20 is connected to the reusable inhaler part in a tappet-like operating condition. In the course of the coupling of the inhaler component with the reusable inhaler part the pin 20 is shifted into the housing 2, as a result of which the first end of the pin 20 presses against the openable catch 19. The openable catch 19 has a material weakening around its periphery which is dimensioned in such a way that when pressure is applied by the pin 20 it tears like a pre-determined breaking point over a substantial region of its periphery, but forms a hinge on one side. In this way the openable catch 19 is caused to open like a flap.

FIGS. 2 to 5 further show a condensate-binding device arranged in the chamber 14 consisting of two open-pored, absorbent sponges 21*a* and 21*b*. The sponges 21*a* and 21*b* absorb into their pores condensate deposits formed from the vapor phase and prevent freely mobile accumulations of condensate from forming in the inhaler component, in particular in the chamber 14, which could impair the function of the inhaler component and, in addition, could represent a risk for the user and the environment, if these accumulations contained drug residues or poisons such as nicotine. The two sponges 21*a* and 21*b* to a large extent line the inner walls of the chamber 14, where the sponge 21*a* extends up to the outlet of the air intake opening 15. In this way the condensate deposits should be prevented from reaching the relatively narrow slot-shaped air intake opening 15, as a result of which the air flow could be obstructed. In an alternative arrangement the air intake opening 15 could also be formed directly by the sponges 21*a* and 21*b*. The sponges 21*a* and 21*b* preferably consist of fine-pored, highly porous fiber composites. The company Filtrona Richmond Inc., www.filtronaporoustechnologies.com, specializes in the production of such fiber composites, in which both triacetin-bonded cellulose acetate fibers and thermally bonded polyolefin and polyester fibers are used.

As shown in FIGS. 2 to 3, a cooler 22 is provided downstream of the sponges 21*a* and 21*b*, which in the specific embodiment is integrated into the preferably interchangeable mouthpiece 3 and consists of a porous wadding 23, through the pores of which the vapor-air mixture or/and condensation aerosol formed flow. The cooler 22 cools the vapor-air mixture or/and condensation aerosol flowing through it and during this withdraws still further condensate from it. In this way the organoleptic characteristics of the vapor-air mixture or/and condensation aerosol taken up by the user can be significantly improved. The wadding 23 can consist for example of a tobacco filling. Such a tobacco filling additionally produces a flavoring of the vapor-air mixture or condensation aerosol flowing through it and is particularly desirable if the liquid material 13 contains nicotine.

Finally, it should be pointed out that the invention is naturally not limited to a laminar composite 5 in accordance with the embodiments just described. The composite could just as well have a linear format.

Furthermore, the composite could also be formed from a plurality of composites or composite sections arranged next to one another, where it is immaterial how the individual composites or composite sections are electrically interconnected to one another. In this connection it should be noted that by means of the multilayer printed circuit board 4 according to the invention both series connections and parallel connections as well as more complex wiring and actuation arrangements can be effected. Finally, the invention also covers devices in which the heating element is arranged separate from the wick. For example, the wick could be formed as a laminate and the heating energy transferred to the wick by electromagnetic waves, in particular radiant heat or microwaves.

LIST OF REFERENCES 1 snap connection
2 housing
3 mouthpiece
4 carrier plate, printed circuit board
5 laminar composite
6 heating element, resistance heating element
7 wick
7*a*, 7*b* end sections of the wick or composite
8*a*, 8*b* plug contacts
9 upper section
10 recess
11*a* first capillary gap
11*b* second capillary gap
11*c* third capillary gap
12 liquid container
12*a* first liquid container
12*b* second liquid container
13 liquid material
14 chamber
15 air intake opening
16*a*, 16*b* ventilation slots
17*a*, 17*b* ventilation holes
18*a*, 18*b* connecting channels
19 openable catch
20 pin
21*a*, 21*b* sponges
22 cooler
23 wadding

The invention claimed is:

1. An inhaler component comprising:
   a heating element configured to evaporate a portion of a liquid material;
   a liquid container for retaining the liquid material, the liquid container comprising a valve which is openable upon coupling of the inhaler component to an inhaler, the opening of the valve allowing the liquid material to be released from the liquid container;
   a wick configured to automatically supply the liquid material to the heating element; and
   a gap configured to automatically supply the wick with the liquid material.

2. The inhaler component according to claim 1, wherein the valve hermetically seals the liquid within the liquid container.

3. The inhaler component according to claim 1, wherein the valve is located on a front face of the liquid container.

4. The inhaler component according to claim 1, wherein the valve has a material weakening around its periphery.

5. The inhaler component according to claim 1, wherein the valve forms a hinge on one side.

6. The inhaler component according to claim 1, wherein the valve is openable like a flap.

7. The inhaler component according to claim 1, wherein the gap is a capillary gap and is further configured to automatically resupply the wick with the liquid material after evaporation.

8. The inhaler component according to claim 1, further comprising a laminar composite including the heating element and the wick, and configured such that liquid in the gap is transferred to the wick via an end section of the laminar composite.

9. The inhaler component according to claim 1, wherein the wick includes a first end section, a second end section, and an intermediate section between the first end section and the second end section, the gap configured to supply the liquid material to at least a portion of at least one of the first end section, the second end section, and the intermediate section.

10. An inhaler comprising:
an inhaler component and a reusable inhaler part, wherein the inhaler component includes:
a heating element configured to evaporate a portion of a liquid material;
a liquid container for retaining the liquid material, the liquid container comprising a valve which is openable upon coupling of the inhaler component to the inhaler, the opening of the valve allowing the liquid material to be released from the liquid container;
a wick configured to automatically supply the liquid material to the heating element; and
a gap configured to automatically supply the wick with the liquid material; and
wherein the reusable inhaler part includes:
a pin configured to open the valve of the liquid container.

11. The inhaler according to claim 10, wherein the gap is a capillary gap and is further configured to automatically resupply the wick with the liquid material after evaporation.

12. The inhaler according to claim 10, further comprising a laminar composite including the heating element and the wick, and configured such that liquid in the gap is transferred to the wick via an end section of the laminar composite.

13. The inhaler according to claim 10, wherein the wick includes a first end section, a second end section, and an intermediate section between the first end section and the second end section, the gap configured to supply the liquid material to at least a portion of at least one of the first end section, the second end section, and the intermediate section.

14. The inhaler according to claim 10, wherein a first end of the pin is directed towards the openable valve during coupling of the inhaler component and the inhaler.

* * * * *